(12) United States Patent
Visser et al.

(10) Patent No.: US 6,675,416 B2
(45) Date of Patent: Jan. 13, 2004

(54) HEAD SUPPORT FOR INTERVENTIONAL MR

(75) Inventors: Frederik Visser, Eindhoven (NL); Johannes Jacobus Van Vaals, Eindhoven (NL); Bartholomeus Muskens, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/837,939

(22) Filed: Apr. 19, 2001

(65) Prior Publication Data

US 2001/0037525 A1 Nov. 8, 2001

(30) Foreign Application Priority Data

Apr. 20, 2000 (EP) ............................................. 00201489

(51) Int. Cl.⁷ ............................................. A61G 13/00
(52) U.S. Cl. .................................. 5/622; 5/621; 5/601
(58) Field of Search ........................... 5/622, 621, 623, 5/624, 658, 503.1, 601; 269/328; 378/208

(56) References Cited

U.S. PATENT DOCUMENTS

| | | | |
|---|---|---|---|
| 4,863,218 A | 9/1989 | McCrackin | 297/39.1 |
| 5,165,137 A | 11/1992 | Amrein et al. | 5/640 |
| 5,276,927 A * | 1/1994 | Day | 5/601 |
| 5,640,958 A * | 6/1997 | Bonutti | 600/415 |
| 6,003,174 A | 12/1999 | Kantrowitz et al. | 5/601 |

FOREIGN PATENT DOCUMENTS

| | | | |
|---|---|---|---|
| DE | G91160022 | 2/1992 | A61G/13/12 |
| EP | 0776637 A1 | 6/1997 | A61B/19/00 |

* cited by examiner

Primary Examiner—Teri Pham Luu
Assistant Examiner—Fredrick Conley
(74) Attorney, Agent, or Firm—John Vodopia

(57) ABSTRACT

In interventional MRI, for example, in neurosurgical applications, the head of a patient must be positioned on a head support while allowing reproducible manipulation of the head. The head support must be made of a material that is compatible with MR. Furthermore, spatial restrictions imposed by the bore of the magnetic resonance apparatus have to be dealt with. The head support in accordance with the invention includes a support whereon the patient head or a stereotactic frame can be rested. The head support is supported by a mounting device. Both the support and mounting device are fixed on the table top. The mounting device provides a sliding surface that enables rotation of the support relative to the mounting device. The support can be curved towards the table top thus providing a concave surface so as to lower the supporting surface for a stereotactic frame and hence to minimize the total volume of the construction. When a radius of between 10 cm and 18 cm is chosen for the sliding surface, the patient will not suffer from stress to the cervical vertebrae during rotation of the supporting means. The reproducibility of the patient positioning with respect to the head support is thus improved, since it is not necessary to reposition the patient after each rotation so as to reduce the induced stress.

20 Claims, 2 Drawing Sheets

HEAD SUPPORT FOR INTERVENTIONAL MR

FIELD OF THE INVENTION

The present invention relates to a positioning system which includes a medical table with a table top and rotation means that can be attached to the table top and which are arranged to accommodate and rotate a part of a patient, the rotation means including supporting means for supporting the part of the patient and mounting means for mounting the rotation means on the table top.

BACKGROUND INFORMATION

A positioning system of this kind is known from EP-A-0 776 637 and is used in the field of stereotactic operations, notably in the field of stereotactic radiosurgery. Radiosurgery involves irradiation of cranial tumors by means of strictly collimated gamma radiation. For reasons of dosimetry it is necessary to position the tumor in the three-dimensional space in such a manner that it can be reached by the gamma radiation from different irradiation angles. The known device utilizes a stereotactic frame that is fixed to a medical table on which a patient is arranged so that the head of the patient projects from the end of the medical table. The stereotactic frame serves to fix the head of the patient and to provide a reproducible rotation of the head of the patient relative to an axis of rotation that is defined by the stereotactic frame. The known device includes a base for supporting the stereotactic frame, said base being mounted on a post on the floor. The rotary motions of the stereotactic frame as a whole are determined by the corresponding motions of the post that acts as a rotation means. Furthermore, the head of the patient can be rotated relative to the axes of rotation that are defined by the stereotactic frame. Because of the construction of the known positioning system it is necessary to use additional supporting means, that is, the combination of a base and the post, in order to support the stereotactic frame as a whole; these additional supporting means bear on the floor.

Meanwhile a need has arisen for the use of such a positioning system for the execution of MR studies of the head of the patient during a neurological intervention. The above-mentioned aspects of the known positioning system make it impossible to use this system for interventional MRI, considering the limited space available in the bore of the MR apparatus and the requirements imposed on the material, notably in respect of MR compatibility. Furthermore, the following supplementary requirements may be imposed as regards the use of the positioning system in the field of neurosurgery: first of all, the physician should have easy access to the region of interest; secondly, if rotation of the stereotactic frame as a whole is necessary, forces exerted so as to realize this rotation should be small and become manifest in the reproducibility of the rotation and the mechanical stability in the rotated position.

OBJECTS AND SUMMARY OF THE INVENTION

It is an object of the invention to provide a positioning system that can be used in the field of interventional MR where neurosurgery is a preferred intervention. To this end, the device in accordance with the invention is characterized in that the mounting means include at least one arc-shaped first guide for guiding the supporting means along the guide, the mounting means extending mainly above a lower surface of the table top.

The positioning system in accordance with the invention does not interfere with the positioning of the patient in the bore of the MR apparatus, because the mounting means of the rotation means are situated mainly above the medical table. Because the rotation means bear on the medical table, the construction of the rotation means is compact and offers the physician excellent accessibility to the cranial regions of the patient. The rotation means in accordance with the invention include the arc-shaped guides for ensuring the rotation of the head of the patient in the cranio-caudal direction.

A first embodiment of the device in accordance with the invention is characterized in that the supporting means include a second guide for co-operation with the first guide, which second guide is practically complementary to the first guide. The use of the complementary first and second guides enhances the mechanical stability of the construction as a whole, considering the enlarged bearing surface for the supporting means.

During the motion of the head of the patient in the cranio-caudal direction, a restriction may occur in respect of the space in the plane above the patient, that is in respect of the admitted volume of the MR apparatus. In order to limit the cylinder enveloping the volume of a patient, a second embodiment in accordance with the invention is characterized in that the supporting means are bent and have a concave surface that faces away from the mounting means in the assembled condition. The shape of the arc of the supporting means can be chosen in such a manner that the supporting point for the patient approaches the table top of the medical table as closely as possible, the volume of the enveloping cylinder thus being minimized. The concave shape of the supporting means provides stable positioning of the head of the patient in the transverse direction in cases where the head rests directly on the supporting means.

Investigations have shown that practically no mechanical stress is exerted on the cervical vertebrae of the patient during rotation of the head in the cranio-caudal direction if the axis of rotation for the rotation in the cranio-caudal direction coincides with the axis of rotation during nodding. Consequently, the patient as a whole need not be positioned again after completion of the rotation of the head. Therefore, for the reproducibility of the head position this rotation is advantageously performed relative to this axis. To this end, a further embodiment is characterized in that the first and the second guide are shaped as an arc of a circle. It has been found that the distance between the head base and the axis of rotation during nodding is in the vicinity of 14 cm for most humans. Therefore, a further embodiment is characterized in that the first guide and the second guide have a radius of between 10 cm and 18 cm. It is an additional advantage that the mechanical balance of the construction as a whole is then also enhanced. It has been demonstrated that the axis of rotation extends through the center of gravity of the head when the axis of rotation of the head coincides with the axis of rotation upon nodding. It is thus ensured that the head also remains balanced in the rotated position. This advantage becomes manifest in the small forces that are necessary to rotate the head, and hence also in the reproducibility of the rotation.

In order to ensure the mechanical stability of the rotation means on the medical table, it may be beneficial for the mounting means to comprise two parts. Therefore, a further embodiment of the device in accordance with the invention is characterized in that the mounting means comprise two substantially parallel first guides. When the rotation means are used in the field of neurosurgery, a stereotactic frame should be fixed on the rotation means. Therefore, a further embodiment of the device in accordance with the invention is characterized in that the supporting means include connection means for fixing a stereotactic frame on the supporting means. The supporting means include, for example a groove in the form of a dovetail, but any other mechanical solution, of course, is also feasible.

As soon as the position of the head or the stereotactic frame has been changed by means of the supporting means, it is desirable to fix the latter means in their ultimate position. Therefore, a further embodiment of the device in accordance with the invention is characterized in that there are provided first fixation means for fixing a rotary position of the supporting means in the mounting means.

Because of safety aspects it must be possible to fix the rotation means on the medical table. To this end, a next embodiment of the device in accordance with the invention is characterized in that there are provided second fixation means for fixing a position of the rotation means on the table top of the medical table.

When the supporting means are curved and approach the table top of the medical table as closely as possible, it may be that a spatial restriction arises in respect of the maximum angle of rotation that can be achieved for the supporting means. Furthermore, at a given angle of rotation the shoulders of the patient collide with the edges of the supporting means. In order to mitigate the spatial restrictions imposed by the supporting means, a further embodiment of the device in accordance with the invention is characterized in that the free edges of the supporting means that extend transversely of the first guide are provided with cut-outs, thus increasing the range of rotation of the supporting means.

These and other aspects of the invention will be described in detail hereinafter with reference to the following embodiments and the accompanying drawing; corresponding reference numerals therein denote corresponding elements.

BRIEF DESCRIPTION ON THE DRAWINGS

DETAILED DESCRIPTION OF THE PREFERED EMBODIMENTS

Figure 1A:
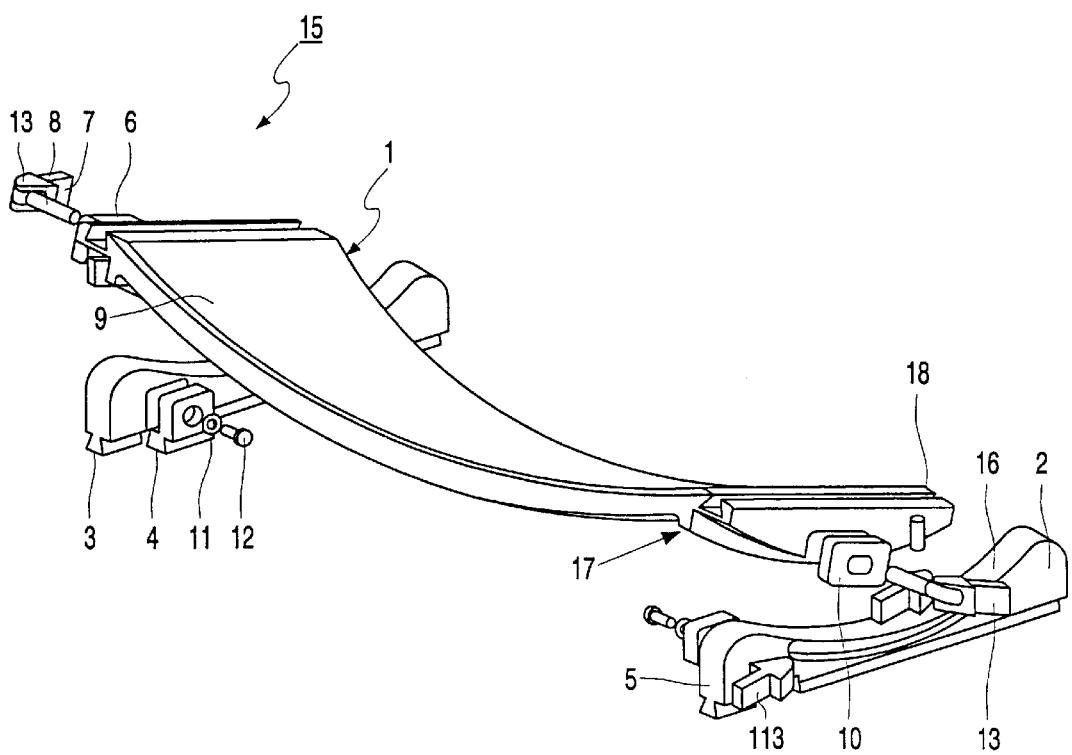
FIG. 1a shows diagrammatically the positioning system in accordance with the invention.
Figure 1B:
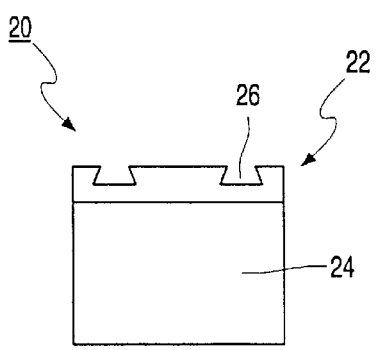
FIG. 1b shows the medical table to which the positioning system is attached.

FIG. 1 shows diagrammatically the positioning system in accordance with the invention; FIG. 1a shows the rotation means in their disassembled condition and FIG. 1b shows a medical table. As is shown in FIG. 1, the positioning system 15 is mounted on a table top 22 that is slidable relative to a table column 24 of the medical table 20. The present example utilizes complementary profiles 3 and 26, that are provided on the mounting means 2 of the rotation system 15 and on the table top 22, respectively. The profiles in the present example are shaped as a dovetail, but the use of other types of profile and other mechanical means, such as clamps and screws, is also feasible. When the complementary profiles are used on the mounting means and the table top, respectively, in addition to mechanical stability of the construction a further advantage is achieved in that no parts project from underneath the table top and hence no spatial restrictions are imposed as regards the bore of the MR apparatus. The mounting means 4 are provided with first guides 16 that are shaped as an arc of a circle; the surface 17 of the supporting means 1 that co-operates with a first guide is shaped as a complementary circle. The surface 17 thus forms a second guide. The guiding of the second guide along the first guide can be realized in a different way by means of rollers which can be arranged between the first guide and the second guide, thus realizing the mutual displacement of the first and the second guide. The use of a circle having a radius of between 10 cm and 18 cm provides the mechanical balance of the head of a patient in the rotation means 15. This is explained by the fact that the axis of rotation for the rotation of the head in the cranio-caudal direction then extends through the center of gravity of the head. As a result only small forces will be required to perform this rotation, and mechanical stability is obtained for this construction in its rotated position. The present example shows the positioning system 15 equipped with two first and two second guides 16 and 17, respectively. However, it is alternatively possible to design a monorail system with only one first guide and only one second guide, the supporting means 1 then bearing on mounting means that are composed of one component only, which component is practically centered relative to the supporting means. The supporting means 1 in the positioning system 15 shown are curved towards the table top 22 of the medical table 20. The use of two first and two second guides offers the physical possibility for bending a surface 9 of the supporting means 1 that is present between the mounting means 2 towards the table top 22. In that case the head of a patient can be positioned as near as possible to the table top 22. The total volume of the enclosure of the patient is thus minimized and the introduction of the overall construction into the bore of the MR apparatus is facilitated. Using the supporting means 1 in accordance with the invention, the head of the patient can be rotated in the cranio-caudal direction in a simple and reproducible manner. This can enhance the accessibility of a region of interest so as to perform a neurological intervention therein. In order to fix a final rotary position of the supporting means 1, the supporting means are provided with first fixation means on both sides, which fixation means consist of a clamp 10 that can be operated by means of an external grip 13. The supporting means 1 are also provided with a groove 18 to enable the mounting of a necessary accessory, for example a stereotactic frame, on the supporting means 1. In order to fix the position of the rotation means 15 as a whole on the table top 22, the mounting means 2 of the positioning system 15 are provided with the second fixation means on both sides. The second fixation means include a clamp 4 whose alignment relative to the dovetail groove 26 of the table top 22 can be changed by means of an external grip 113. As soon as the alignment of the second fixation means has been changed, they act as a clamp in the longitudinal direction of the groove 26.

Figure 2:
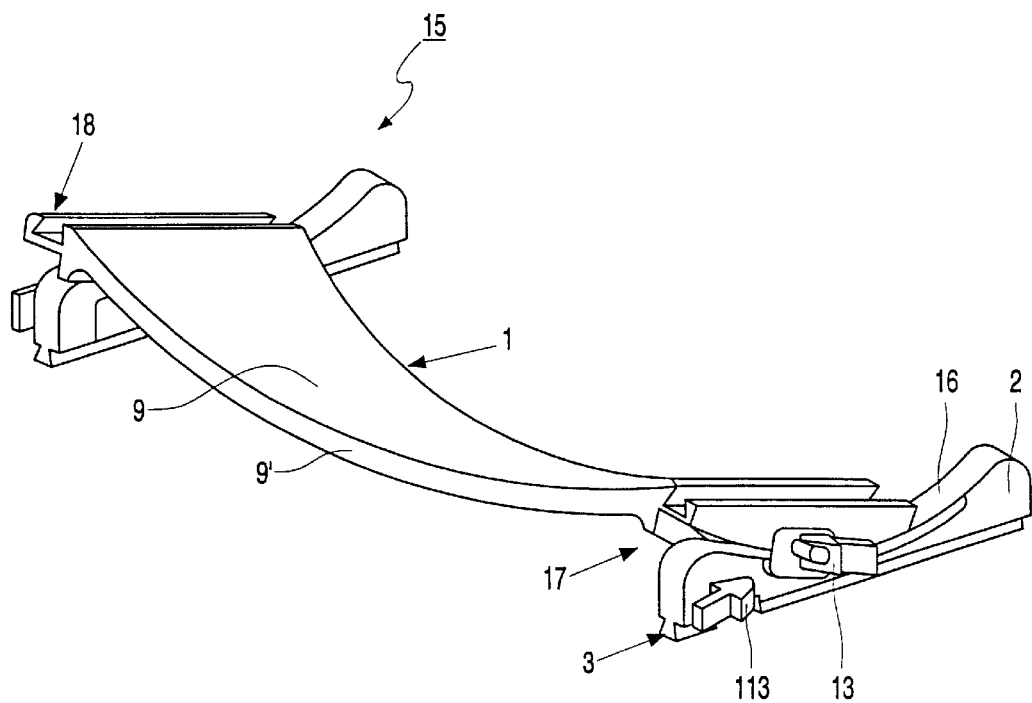
FIG. 2 shows diagrammatically rotation means in accordance with the invention in the assembled condition.

FIG. 2 diagrammatically illustrates the rotation means 15 in accordance with the invention in the assembled condition. The supporting means 1 bear on the mounting means 2. The first and second guides 16, 17 provide the reproducible rotation in the cranio-caudal direction. A rotary position of the supporting means 1 relative to the mounting means 2 can be fixed by means of the first fixation means that can be operated by way of the grip 13. The rotation means 15 can be fixed to the table top of the medical table (not shown in FIG. 2) by means of a groove 3. The second fixation means can be operated by means of the grip 113 and fix the position of the rotation means 15 as a whole relative to the table top.

In order to enable the necessary accessories to be mounted on the supporting means 1, the latter means are provided with a groove 18.

Figure 3:
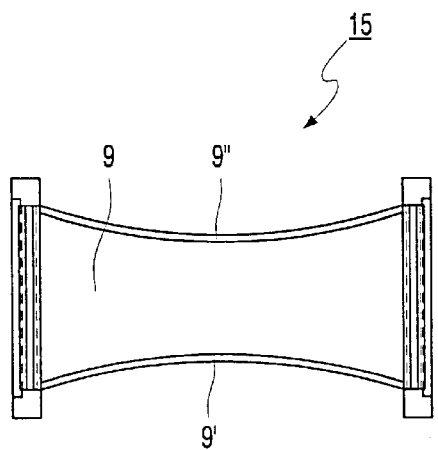
FIG. 3 is a diagrammatic plan view of the rotation means, the supporting means being provided with cut-outs.

When the surface 9 of the supporting means 1 is curved in the direction transversely of the mounting means 2 and approaches the table top as closely as possible, it could be that physical restrictions are imposed as regards the rotation of the supporting means 1. In order to avoid a collision between the edges 9' of the supporting means 1 and the table top and/or the shoulders of the patient, the surface 9 of the supporting means 1 is provided with cut-outs 9" that are shown diagrammatically in FIG. 3.

What is claimed is:

1. A positioning system including a medical table having a table top including upper and lower surfaces, comprising:
    rotation means operatively selectably mounted to the table top and arranged to accommodate and rotate a part of a patient, the rotation means including supporting means for supporting the part of the patient and mounting means for mounting the rotation means to the table top, wherein the mounting means includes at least one arc-shaped first guide slidably engaged with the supporting means for guiding the supporting means along the mounting means wherein, the supporting means includes a second guide which cooperates with the first guide, the first and second guides contacting one another and slidably engaging to alter the orientation of the supporting means.

2. The positioning system as defined by claim 1 wherein said second guide being substantially complementary to the first guide.

3. The positioning system as defined by claim 2 wherein the first and the second guides are arc-shaped.

4. The positioning system as defined by claim 3 wherein the first and the second guides have a radius of curvature between 10 cm and 18 cm.

5. The positioning system as defined by claim 1 wherein the supporting means is non-linear and has a concave surface which faces away from the mounting means in an assembled condition.

6. The positioning system as defined by claim 1 wherein the mounting means comprises first and second substantially parallel arc-shaped first guides.

7. The positioning system as defined by claim 1 wherein the supporting means comprises connection means for coupling a stereotactic frame to the supporting means.

8. The positioning system as defined by claim 1 further comprising fixation means for fixing a rotary position of the supporting means.

9. The positioning system as defined by claim 1 further comprising fixation means for fixing a position of the rotation means on the table top of the medical table.

10. The positioning system as defined by claim 1 wherein the supporting means includes free edges that extend transversely with respect to the first guide, the supporting means also including a concave surface in order to increase the range of rotation of the supporting means.

11. The positioning system as defined by claim 1 wherein the mounting means extends mainly above the lower surface of the table top.

12. The positioning system as defined by claim 11 wherein the mounting means extends only above the lower surface of the table top.

13. A head support system for an interventional MR, comprising:
    rotation means operatively selectably mounted to a table top of a medical table, the table top having upper and lower surfaces, the rotation means being arranged to accommodate and rotate a part of a patient, the rotation means including supporting means for supporting the part of the patient and mounting means for mounting the rotation means to the table top, wherein the mounting means includes at least one arc-shaped first guide slidably engaged with the supporting means for guiding the supporting means along the mounting means wherein, the supporting means includes a second guide which cooperates with the first guide, the first and second guides contacting one another and slidably engaging to alter the orientation of the supporting means.

14. The positioning system as defined by claim 13 wherein said second guide being substantially complementary to the first guide.

15. The positioning system as defined by claim 14 wherein the first and the second guides are arc-shaped.

16. The positioning system as defined by claim 15 wherein the first and the second guides have a radius of curvature between 10 cm and 18 cm.

17. The positioning system as defined by claim 13 wherein the supporting means is non-linear and has a concave surface which faces away from the mounting means in an assembled condition.

18. The positioning system as defined by claim 13 further comprising fixation means for fixing a position of the rotation means on the table top of the medical table.

19. The positioning system as defined by claim 13 wherein the supporting means includes free edges that extend transversely with respect to the first guide, the supporting means also including a concave surface in order to increase the range of rotation of the supporting means.

20. The positioning system as defined by claim 13 wherein the mounting means extends mainly above the lower surface of the table top.

* * * * *